(12) United States Patent
Faris

(10) Patent No.: US 6,786,610 B2
(45) Date of Patent: Sep. 7, 2004

(54) GLARE BLOCKING DEVICE

(75) Inventor: Sadeg M. Faris, Pleasantville, NY (US)

(73) Assignee: InventQjaya Sdn. Bhd., Cyberjaya (MY)

( * ) Notice: Subject to any disclaimer, the term of this patent is extended or adjusted under 35 U.S.C. 154(b) by 0 days.

(21) Appl. No.: 10/141,097

(22) Filed: May 7, 2002

(65) Prior Publication Data

US 2004/0012762 A1 Jan. 22, 2004

Related U.S. Application Data

(60) Provisional application No. 60/288,675, filed on May 7, 2001.

(51) Int. Cl.$^7$ .............................................. G02B 27/00
(52) U.S. Cl. ...................... 359/613; 359/601; 359/604; 359/608
(58) Field of Search ................................ 359/613, 601, 359/604, 608; 347/7, 8, 9, 84, 105

(56) References Cited

U.S. PATENT DOCUMENTS

| | | | | | |
|---|---|---|---|---|---|
| 5,305,012 | A | * | 4/1994 | Faris | 345/7 |
| 5,841,507 | A | * | 11/1998 | Barnes | 351/49 |
| 6,133,947 | A | * | 10/2000 | Mikuni | 348/143 |
| 6,270,223 | B1 | * | 8/2001 | Del Bon et al. | 359/601 |
| 6,394,614 | B1 | * | 5/2002 | Chang | 359/604 |
| 6,483,090 | B1 | * | 11/2002 | Bae | 250/201.1 |
| 6,528,782 | B1 | * | 3/2003 | Zhang et al. | 250/226 |

* cited by examiner

Primary Examiner—Mohammad Sikder
(74) Attorney, Agent, or Firm—Ralph J. Crispino

(57) ABSTRACT

An apparatus is provided for automatically reducing glare produced from a spatial scene by reducing the intensity of light rays propagating from points in the three-dimensional spatial scene towards an optical element having a field of view. Further, an apparatus is provided that automatically reduces interfering illumination produced from an illumination source by reducing the intensity of light rays propagating from the illumination source towards a sensor having a field of view of radio communication. Both apparatus include an electro-optical element having an optically transparent surface including a plurality of pixels through which the field of view of the optical element or the sensor passes. Each pixel has a controllable light transmittance for selectively reducing the intensity of incident light rays propagating from one or more points from the illumination source, through the pixel, then towards the sensor or optical element. An image acquisition device is included for acquiring one or more images of the illumination source within the field of view of the sensor or optical element. A processor is also included for processing the acquired images and determining at which pixels the light transmittance is to be actively controlled in order to reduce the intensity of incident light rays before reaching the sensor or optical element. A control is also provided for actively controlling the light transmittance of the determined pixels so that after incident light rays propagate through the determined pixels, the incident light rays propagate towards the sensor or optical element with reduced intensity.

17 Claims, 4 Drawing Sheets

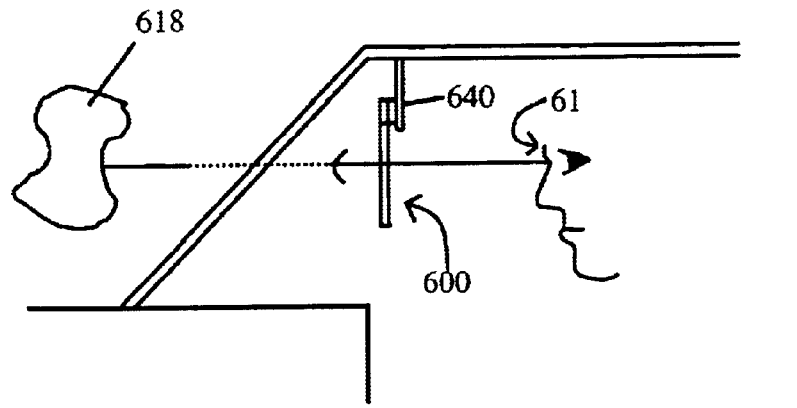
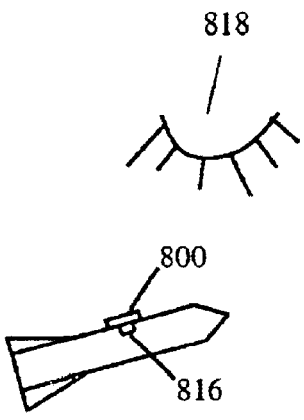
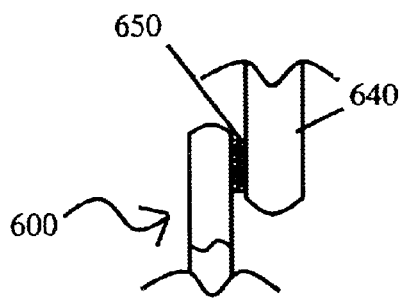
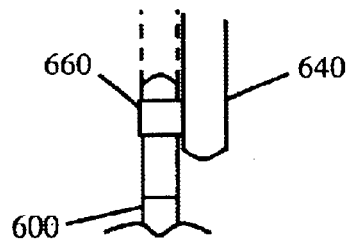
Figure 6A
Figure 8
Figure 6B
Figure 6C
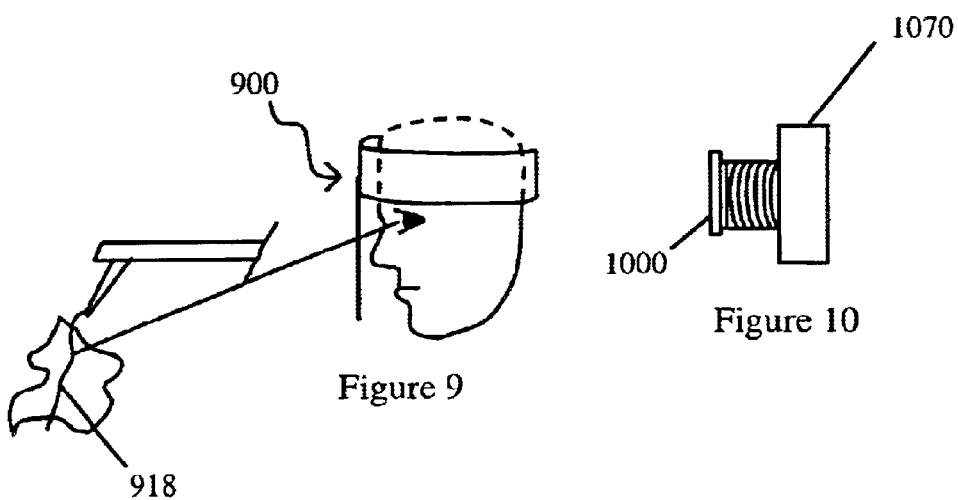
Figure 9
Figure 10

GLARE BLOCKING DEVICE

RELATED APPLICATIONS

The present invention claims priority to U.S. Provisional Patent Application Serial No. 60/288,675 entitled "Glare Blocking Device" filed on May 7, 2001, which is hereby incorporated by reference in its entirety.

BACKGROUND OF THE INVENTION

1. Field of the Invention

The present invention generally relates to glare blocking device, and particularly to an integrated device that selectively reduces the intensity of incident light as is propagated toward an optical element.

2. Description of the Prior Art

Many sources of illumination producing glare which detrimentally affects various types of optical systems. For example, many outdoor activities are effectuated more comfortably with the use of sunglasses, particularly in times of extreme sunlight. However, with use of conventional sunglasses, all visible light intensity is reduced. This may be problematic, for example, in areas of shade, or, for example, while driving in the less illuminated areas such as trials.

Further, even in at night, artificial light, such as from headlamps of oncoming cars, is propagated onto the eyes of automobile drivers. This is particularly problematic when the headlamps are in high-beam mode, such that the driver is essentially unable to view the road ahead. Additionally, many vehicles are equipped with high-intensity headlamps which have a high-intensity under normal operation, and even higher intensity under high-beam mode of operation. As a driver continues to view the intense headlamps, the driver's division becomes fatigued, consequently impairing their ability to drive effectively.

Also, with the increase in popularity in laser corrective surgery, many individuals are becoming increasingly sensitive to glare associated with sunlight or artificial light.

Therefore, it will be desirable to provide an efficient and convenient system that solves the above-mentioned problems.

SUMMARY OF THE INVENTION

The present invention provides an apparatus for automatically reducing glare produced from a spatial scene by reducing the intensity of light rays propagating from points in the three-dimensional spatial scene towards an optical element having a field of view. The apparatus includes an electro-optical element having an optically transparent surface including a plurality of electrically addressable pixels through which the field of view of the optical element passes. Each pixel has a controllable light transmittance for selectively reducing the intensity of incident light rays propagating from one or more points in the spatial scene, through the pixel, then towards the optical element. The apparatus also includes an image acquisition device for acquiring one or more images of the spatial scene within the field of view of the optical element. A processor is also provided for processing the one or more acquired images and determining at which pixels the light transmittance is to be actively controlled in order to reduce the intensity of incident light rays by a selected amount before reaching the optical element. Further, a control is provided for actively controlling the light transmittance of the determined pixels so that after incident light rays propagate through the determined pixels, the incident light rays propagate towards the optical element with an intensity reduced by the selected amount, so that glare produced from the spatial scene is automatically reduced. To provide for convenient and portable operation of the apparatus, a power supply may be integrated within the apparatus for providing electrical power to the image acquisition device, the processor, and control.

The above-discussed and other features and advantages of the present invention will be appreciated and understood by those skilled in the art from the following detailed description and drawings.

BRIEF DESCRIPTION OF THE DRAWINGS

FIGS. 6A–6C depict a glare blocking device used in an automobile and various attachments;

FIG. 8 depicts a glare blocking device incorporated within an aerospace vehicle tracking system;

FIG. 9 depicts a glare blocking device incorporated within a welding mask; and

FIG. 10 depicts a glare blocking device incorporated with a camera.

DETAILED DESCRIPTION OF THE ILLUSTRATIVE EMBODIMENTS

Figure 1:
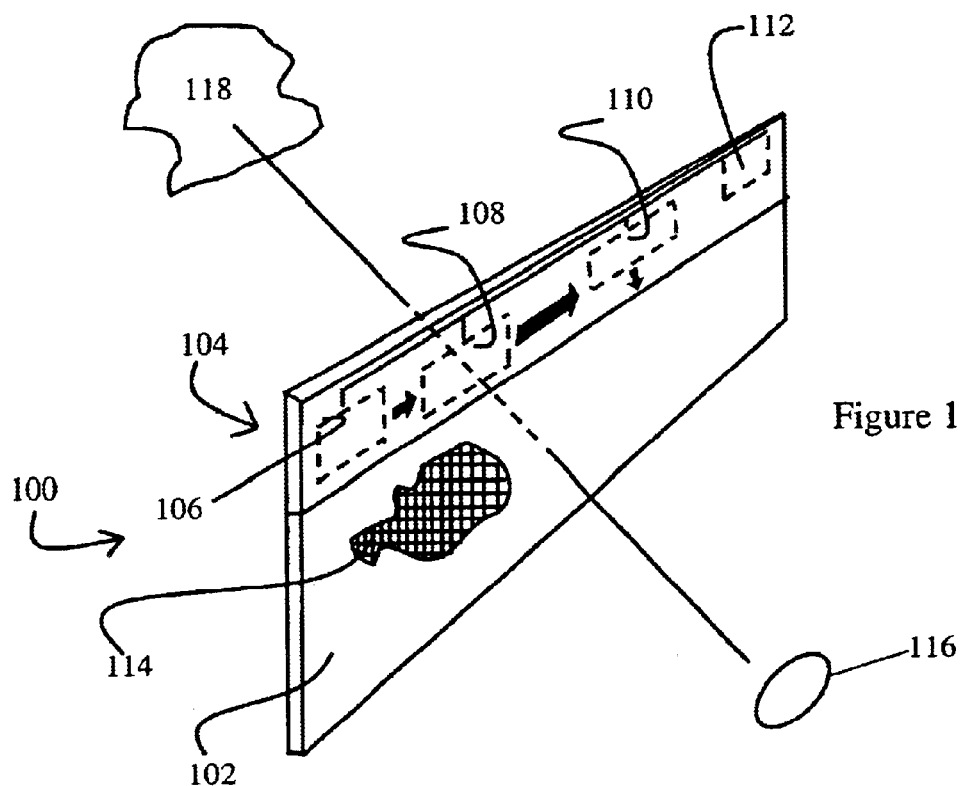
FIG. 1 shows a general embodiment of the glare blocking device.

Referring now to FIG. 1, a general embodiment of a glare blocking device 100 is depicted. Glare blocking device 100 includes an electro-optical element 102 and a control and power system 104. The control and power system 104 includes therein an image acquisition device 106, a processor 108, a control 110, and a power supply 112. All of the components of the glare blocking device according to this embodiment are integrated into a wireless apparatus. This wireless apparatus conveniently may be employed in a variety of applications, including, but not limited to, automobile visors, glasses, masks, attachments (e.g., 40 camera), shades (e.g., as in on the side windows of automobile, such as to prevent glare and other excess illumination to passengers within the automobile), and the like.

The electro-optical element 102 comprises a plurality of pixels 114. During operation, an optical element 116 is in optical communication with an illumination source 118. If the illumination source 118 is above a preselected or adjustably preselected value (generally as determined by the image acquisition device 106 and the processor 108, as in further described herein), the control 110 will address one or more pixels 114 associated with the location of the illumination source 118. Such operation is described in detail in U.S. Pat. No. 5,305,012 entitled "Intelligent Electro-Optical System and Method for Automatic Glare Reduction" by the applicant herein, which is incorporated by reference herein in its entirety.

Each of the pixels 114 is electronically addressable by the control 110, and has a light transmittance which is actively controllable for the purpose of selectively reducing the intensity of an incident light ray propagating from a point of illumination source 118 in the spatial scene, through the pixel, towards the optical element 116. Typically, points on the surface of electro-optical element 102 are measured with respect to a coordinate system. The coordinate system may be a Cartesian coordinate system specified by principal coordinate axes x, y and z, a polar coordinate system, or any other type of coordinate systems.

Preferably, the pixels along the transparent surface are formed from a polymer-dispersed liquid crystal film having a light transmittance of at least 70% in the optical spectrum, that is, when the pixels are not actively controlled or driven by control 110. Each pixel located on the optically transparent surface at coordinates (x, y) is electrically addressable by an address value A(x,y) computed by the processor 108. When driving an addressed pixel or set of pixels at any particular instant in time, the intensity (i.e. brightness) of incident light rays transmitted along the line of sight through these actively driven pixels is reduced by a selected amount which is sufficient to achieve effective reduction of glare produced in diverse environments. The degree of intensity reduction achievable at each pixel can be of a binary nature (i.e., a first light transmittance when not actively driven, or a lesser light transmittance when actively driven). Alternatively, the degree of intensity reduction m(x, y) can be quantized to one of a number of possible states. For further details regarding suitable polymer-dispersed liquid crystal films that may be used in practicing the present invention, reference is made to the following publications: "Reverse-Mode MicroDroplet Liquid Crystal Display" by Y. D. Ma and B. G. Wu, on pages 46–57, SPIE Vol. 1257, Liquid Crystal Displays and Application (1990); and "Polymer-Dispersed and Encapsulated Liquid Crystal Films", by G. Paul Montgomery, Jr., on pages 577–606, SPIE Institute Series Vol. IS4, Large-Area Chromogenics: Materials and Devices for Transmittance Control 1990, which are hereby incorporated by reference.

In general, the image acquisition device 106 includes at least one opto-electronic sensor. The sensor may be realized in the form of image forming optics, CCD, CMOS, or a combination of at least one of the foregoing opto-electronic sensors. The sensor generally includes an array of pixels such that it may be coordinated with the pixels 114 on the electro-optical element 102. The image acquisition device 106 is used to generate an electronic image signal of the spatial scene. The coordinates of pixels on the array of the image acquisition device are measured with respect to a coordinate system, preferably compatible with the coordinate system used for the pixels of the electro-optical element 102. The principal function of the camera station is to acquire images of the spatial scene within the field of view of the optical element 116.

Processor 108 may comprise a microcomputer system having associated memory for buffering acquired images. The microcomputer processes the acquired image(s) from the camera station in order to determine at which pixels 114 in the electro-optical element 102 the light transmittance is to be actively controlled (the "controlled pixels 114") in order to reduce the intensity of incident light rays by a selected amount before they reach the optical element 116. The processor 108 produces intensity reduction data representative of the selected amount of intensity reduction at the controlled pixels 114. In further embodiments, the image acquisition device 106 and the processor 108 (or a portion thereof) may be integrally embedded within a CMOS camera.

The control 110 generally comprises controller/driver circuitry interfaced with the processor 108. The principal function of control 110 is to automatically address controlled pixels 114 and actively control the light transmittance thereof accordance with intensity reduction data. In this way, as light rays propagate from the spatial scene and through the actively controlled pixels in electro-optical element 102, the incident light rays propagating through these pixels will reach the optical element with an intensity that has been reduced by the selected amount of light transmittance. The selected amount of light transmittance may vary depending on the particular application, depending on circumstances and usage of the glare blocking device 100.

The power supply 112 may be realizable as a suitable power converter (e.g., DC-DC or AC-DC), a primary battery, a secondary battery, a solar cell, or combinations thereof. For example, suitable power converters and/or solar cells may be associated with a secondary battery for recharging of the secondary battery. The principal function of the power supply 112 is to provide power to the image acquisition device 106, the processor 108, and the control 110. Preferably, the power supply 112 is suitably configured and dimension for the particular glare blocking the device 100. For example, in the case of a visor, for attachments to an automobile sunvisor, the power supply 112 may comprise a secondary (i.e., rechargeable) battery. The battery (or plurality of batteries) may be recharged by an external power source, such as a home or automobile charger. Further, the power supply 112 may include one or more secondary batteries and one or more solar cells. The solar cells may serve to recharge the secondary batteries and/or provide power to other components of the control and power system 104.

In one embodiment, where a solar cell is used, for example, in conjunction with a secondary battery, the solar cell may be disposed in a suitable location on the glare blocking device 100 that is exposed to sufficient illumination to allow the solar cell to charge the secondary battery. For example, where the glare blocking device 100 is embodied as an attachment to the visor in an automobile, as described in more detail herein, the solar cell may be located on the side of the glare blocking device 100 that faces the windshield. In this manner, the solar cell receives optimum illumination to provide energy for operation and charging, and further the solar cell 100 may be used when the device is stowed away, for example, as described in FIG. 6C further herein. Thus, the secondary battery may be continuously charged by the solar cell. Suitable controls or electronics may also be provided to prevent overcharging of the secondary battery.

Figure 2:
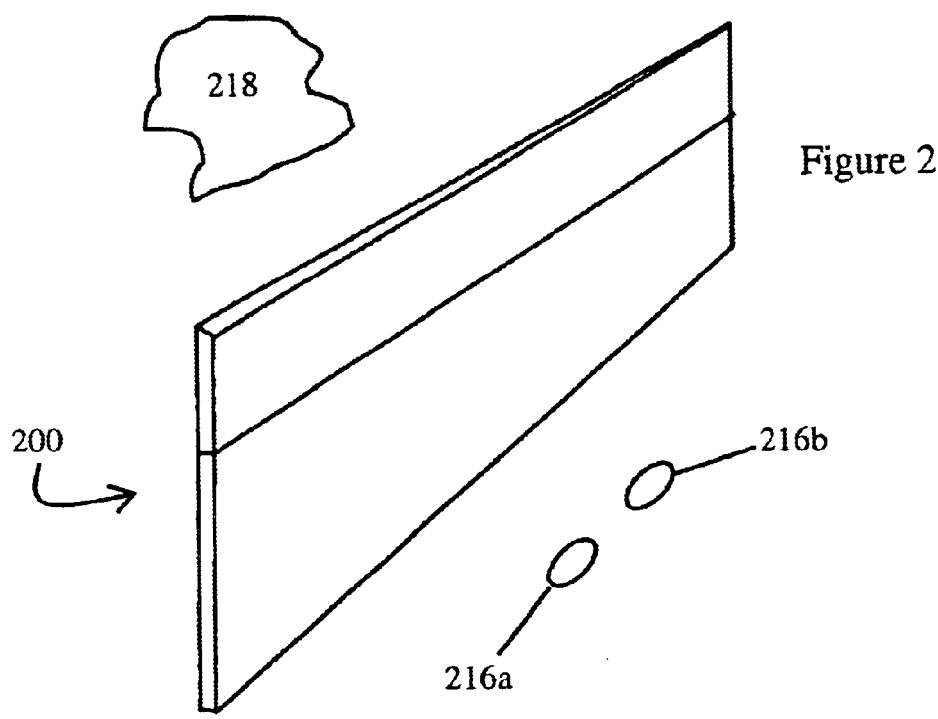
FIG. 2 schematically depicts a glare blocking device associated with a pair of optical elements.

Referring now to FIG. 2, a glare blocking device 200 is schematically depicted. A pair of optical elements 216a, 216b are provided. The pair of elements (e.g., a pair of pupils) are provided so as to describe operation of the glare blocking device 200 in stereoscopic mode. In one embodiment, the device 200 may incorporate a pair of image acquisition devices, each operating generally as described above with respect to the image acquisition device 116. Each image acquisition device may view the imaging based on the field of view of each respective optical elements 216a, 216b. In this mode, each image acquisition device "sees" what each optical elements 216a, 216b "sees". To determine the position of each optical elements 216a, 216b, a pair of infrared cameras may be employed with their optical axes directed toward the optical elements 216a, 216b, for example, to form a pupil-tracking camera subsystem which measures the position of the optical elements 216a, 216b (e.g., pupils) relative to the pixels of the electro-optical elements. Techniques for determining the position of optical elements such as pupils from an acquired pair of stereo infrared images are well-known in the art, and are described in detail, for example, in Chapter 13, "Photogrammy and Stereo", on pp 299–327, of Robot Vision (1991) by Berthold Klaus Paul Horn, published by MIT Press, Cambridge, Mass. Further, depth-map data (i.e., x, y and z coordinates) of each point in the spatial scene viewed by the optical elements 216a, 216b can be readily computed, for example, as described in the above-mentioned reference.

Figure 3:
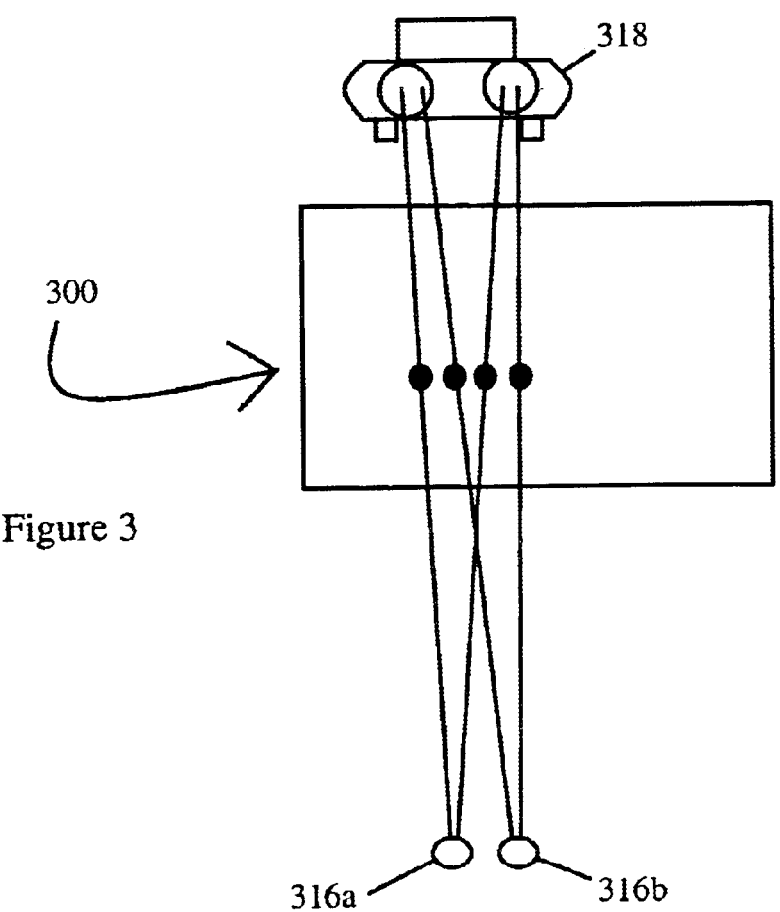
FIG. 3 schematically depicts a glare blocking device associated with a pair of optical elements and a pair of illumination sources.

Referring now to FIG. 3, another embodiment of a glare blocking device 300 is schematically depicted. In this embodiment, a pair of optical elements 316a, 316b are depicted. Further, a source of illumination 318 is realized in the form of an automobile with a pair of headlights directing a high intensity illumination to the optical elements 316a, 316b. Therefore, since there are a pair of optical elements, and a pair of high intensity illumination sources, four regions of one or more controlled pixels are addressed by the control corresponding with the left and right headlamps as viewed by the left-handed optical element, and the left and right headlands as viewed by the right-handed optical element. The glare blocking may be effectuated as described generally above with respect to FIG. 2, utilizing a pair of image acquisition devices. In a further embodiment, to simplify the overall elements of the system, a single image acquisition device may be provided. During processing of the acquired image, the pair of regions of one or more controlled pixels (associated with each optical element 316a, 316b) may be controlled based upon the distance between the two optical elements 316a, 316b. In this matter, a single image acquisition device may be utilized, which preferably "sees" the field of view of the pair of optical elements at the midpoint between the pair of optical elements. The distance between the two optical elements may be preprogrammed in the processor (e.g., 1.25 inches to the right and 1.25 inches to the left, based on an average distance between two human eyes of 2.5 inches). Alternatively, the distance between the pair of optical elements 316a, 316b may be calibrated. For example, the device 300 may be equipped with an input system operably coupled to the processor, whereby the user may enter the distance between his or her eyes. Further, the device 300 may be equipped with an integral or separate eye tracking device, which automatically measures the distance between the pupils of the user. Such an eye tracking system may operate one time (e.g., when the used initially sets up the glare blocking device), each time the glare blocking device is used at start-up, intermittently, or continuously.

As an alternative to using an eye tracking device to determine the field of view of the user, a calibration system can be used based generally on approximations. A calibrating object (e.g., an object recognizable by the image acquisition device) may be located at a point behind the glare blocking device. When the object is at a position at which the user can view (e.g., without impairment of the glare blocking device), the system may be automatically calibrated. For example, the image acquisition device may determine the presence of the object, and then determine the location of the object by recognizing the object within the acquired image (e.g. by the processor). The processor may be suitably programmed to approximate the position of the users pupils, generally based on the known dimensions of the blocking device and other parameters, such as the distance of the calibration object to the device and/or the distance of the user from the device. These distance is may be: programmed (e.g., approximated values based on various types or models of vehicles); user imported (e.g. whereby the user imports the distance of the object from a point on declare blocking device, and the user imports the approximate distance of the users eyes to the glare blocking device); or a combination thereof.

Figure 4:
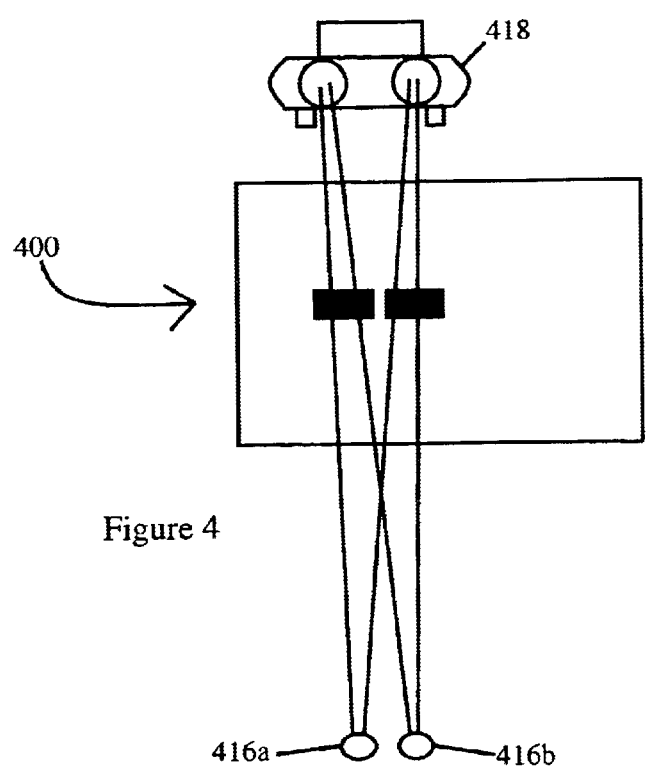
FIG. 4 schematically depicts a glare blocking device associated with a pair of optical elements and a pair of illumination sources and a simplified system for glare blocking.

Referring now to FIG. 4, a glare blocking device 400 is depicted, wherein optical elements 416a and 416b are in optical communication with a high intensity illumination sources 418, which includes a pair of illumination sources. In this embodiment, instead of the controller addressing two regions of one or more controlled pixels based on each illumination source (i.e., four regions of one or more controlled pixels as depicted in FIG. 4), one region of one or more controlled pixels may be addressed, which generally corresponds to one optical elements 416a or 416b. Therefore, for example, as depicted in FIG. 4, for a pair of high intensity illumination sources and a pair of optical elements (e.g., a pair of headlights and a pair of eyes), two regions of one or more controlled pixels may be blocked instead of four regions of one or more controlled pixels.

Figure 5:
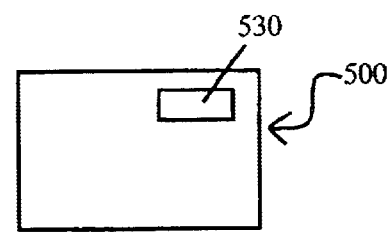
FIG. 5 schematically depicts a glare blocking device having a controllably reflective portion thereof.

In a still further embodiment of the present intention, and referring now to FIG. 5, a glare blocking device 500 may incorporate an electro-optical device 530 having reflection, semi-transparent, and transparent modes of operation, as fully described in U.S. Pat. No. 6,072,549 entitled "Intelligent Glazing Structures With Additional Controlled Layers", by Faris et al., which is incorporated by reference herein in its entirety. With the inclusion of the electro-optical device 530, the user may selectively switch the device 530 between a reflective state and a default state. In the default state, the region occupied by the electro-optical device 530 is similar to, for example, the electro-optical elements 102. That is, upon attainment of certain values of illumination sources, the region occupied by the device 530 is "semi-transparent", wherein at least a portion of the incident light rays are blocked.

The level of intensity of the incident light rays upon which the blocking device herein is activated (e.g., wherein one or more regions of one or more controlled pixels are operably addressed by the control) may be predetermined based on commonly accepted intensity levels for sunlight, headlights, or other illumination source (e.g., a torch, a UV light source, etc.). Also, the value may be preselected by the user with an input device coupled to the processor. This allows for sensitivity variations for individuals.

Alternatively, the level of intensity of the incident light at which the blocking device is activated may be relative. That is, the image acquired by the image acquisition device may be scanned for an average illumination intensity, and regions that are a certain value above the average illumination intensity may be blocked or reduced. Further, the relative values may be based on the relationship between a plurality of regions of one or more pixels. For example, the processor may determine that the region of one or more pixels is much greater than an adjacent region of one or more pixels (wherein the difference may be preselected e.g., five times greater).

Referring now to FIG. 6A a blocking device 600 may be incorporated in an automobile, for example, by attachment to an existing visor 640 in the automobile. The attachment to the blocking device 600 to the visor 640 may be effectuated in a removable, permanent, or adjustable matter. In a permanent manner, the glare blocking device 600 may be attached to the visor 640 with suitable fasteners, such as adhesive and/or screws. In a removable fashion, the glare blocking device 600 may be removably attached to the visor 640 by clips, hook and loop fasteners, or other suitable removable fasteners. For example, FIG. 6B depicts the glare blocking device 600 removably attached to the visor 640 with a removable fasteners 650, such as a corresponding pair of hoop and loop fasteners, or a clip.

Further, and referring now to FIG. 6C, the glare blocking device 600 may be adjustably attached to the visor 640 with an adjustable system 660. The adjustable system 660 may comprise, for example, a suitable track system, or a U-shaped fastener that facilitates a frictional engagement between the glare blocking device 600 and the visor 640. In this manner, the glare blocking device 600 may be positioned up or down, to adjust the height of the glare blocking device when used, or to suitably stow away the glare blocking device behind the visor 640 when not in operation.

Another embodiment of adjustably attached glare blocking device includes a motorized system for moving the glare blocking device 600 up and down. The motorized system may be semi-automatic, e.g., whereby a user pushes a button such that the glare blocking device 600 advanced or detract. Further, the system may be automatic, whereby the image acquisition device and processor continue to operate in the retracted position, and wherein upon detection of a certain intensity of incident light, the blocking device 600 automatically advances. The system may further include an override, for example, so that the user may prevent advancement of the blocking device 600.

Figure 7:
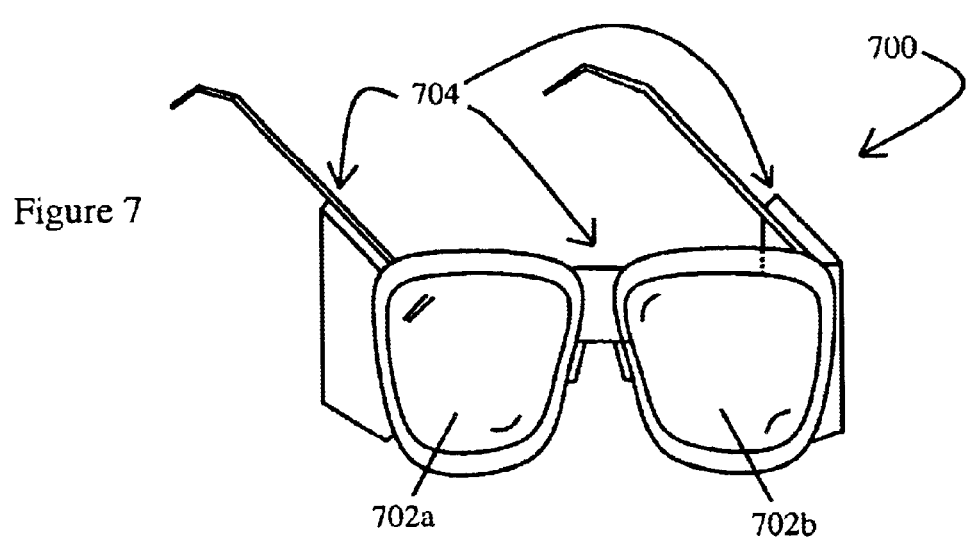
FIG. 7 depicts a glare blocking device incorporated within eyeglasses.

Referring now to FIG. 7, a glare blocking device 700 is realized in the form of a pair of eyeglasses. Each lens of the pair of eyeglasses, or a portion thereof, comprises electro optical elements 702a and 702b. The control and power system 704 may be positioned in any convenient location on the eyeglasses, such as on the sides of the eyeglasses, proximate to the bridge of the eyeglasses, or a combination thereof. Preferably, the image acquisition device is located in proximate to the bridge portion of the eyeglasses, to simplify processing and control of the image. Alternatively, one or more sensors, such as radio frequency sensors, may be integrated into the control and power system 704, which may wirelessly communicate with an external control and/or processor.

Referring now to FIG. 8, a glare blocking device 800 is incorporated in an airplane, spacecraft, missile, or other various manned or unmanned land, sea, and aerospace vehicles having one or more optical elements 816 realized in the form of a tracking sensor. The glare blocking device 800 may be used to block or limit certain high intensity sources that may interfere with communication (e.g., radio frequency communication) of the tracking sensors. Such tracking sensors are commonly used for tracking of various manned and unmanned land, sea, and aerospace vehicles, such as automobiles, trucks, water vessels, missiles and airplanes.

During travel, the tracking sensor may encounter high intensity sources such as excessive sunlight. In this case, the excessive sunlight essentially saturated to the tracking sensor, minimizing or disabling the functionality thereof. While the missile is traversing regions of high intensity sunlight from illumination source 818 (e.g., the sun), the device 800 may operate to minimize or eliminate detrimental effects related to tracking of the missile.

Referring now to FIG. 9, a glare blocking device 900 may be realized in the form of a shield or a portion of a shield, for example, for use as a welding mask. The control and power system 904 may be conveniently located, for example, on a portion of the headband for the welding mask. Alternatively, or in conjunction with that location for the control and power system 904, a portion of the control and power system such as the image acquisition device may be integrated in the front portion of the glare blocking device 900, for example, proximate to the wearer's forehead. This allows for convenient image processing.

Referring now to FIG. 10, the glare blocking device 1000 may be realized in the form of a lens attachment for a camera 1070, such as a still or video camera.

It should be noted that a variety of other auxiliary electronic devices may be incorporated in the glare blocking device described herein. For example, a global positioning system may be included, which may be powered by the power supply of the glare blocking device.

The blocking device described herein, and its various embodiment, may be realized as a wireless device. This allows the glare blocking device to conveniently be utilized in situations with which otherwise would be inconvenient. For example, an automobile, the use of wires may be inconvenient.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. Apparatus for automatically reducing glare produced from a spatial scene by reducing the intensity of light rays propagating from points in the three-dimensional spatial scene towards an optical element having a field of view, said apparatus embodied within a structure for attachment to a visor in a vehicle said apparatus comprising:

an electro-optical element having an optically transparent surface including a plurality of pixels through which the field of view of said optical element passes, each said pixel having a controllable light transmittance for selectively reducing the intensity of incident light rays propagating from one or more points in the three-dimensional spatial scene, through said pixel, then towards said optical element;

an image acquisition device for acquiring one or more images of said three-dimensional spatial scene within the field of view of said optical element;

a processor for processing said one or more acquired images and determining at which pixels the light transmittance is to be actively controlled in order to reduce the intensity of incident light rays by a selected amount before reaching said optical element;

a control for actively controlling the light transmittance of the determined pixels so that after incident light rays propagate through said determined pixels, said incident light rays propagate towards said optical element with an intensity reduced by said selected amount, so that glare produced from the spatial scene is automatically reduced; and said structure configured and dimensioned for attachment to said visor in said vehicle.

2. The apparatus is in claim 1, further comprising a power supply integrated within the apparatus for providing electrical power to the image acquisition device, the processor, and control.

3. The apparatus is in claim 2, when the power supply comprises a primary battery.

4. The apparatus is in claim 2, when power supply comprises a secondary battery.

5. The apparatus is in claim 4, when the secondary battery is recharged by an external power source.

6. The apparatus is in claim 4, wherein said secondary battery is recharged by a solar cell within the apparatus.

7. The apparatus is in claim 2, wherein the power supply comprises a solar cell.

8. The apparatus is in claim 1, further comprising an auxiliary electronic device.

9. The apparatus is in claim 8, wherein the auxiliary electronic device comprises a global positioning system.

10. The apparatus is in claim 2, further comprising an auxiliary electronic device.

11. The apparatus is in claim 10, wherein the auxiliary electronic device comprises a global positioning system.

12. The apparatus as in claim 1, configured and dimensioned for removable attachment to a visor in a vehicle.

13. The apparatus as in claim 1, configured and dimensioned for adjustable attachment to a visor in a vehicle.

14. The apparatus as in claim 1, configured and dimensioned for adjustable attachment to a visor in a vehicle, further comprising a motorized system for moving at least a portion of the apparatus into and out of the field of view of the optical element.

15. The apparatus as in claim 1, wherein the structure for attachment to a visor in a vehicle is configured and dimensioned for removable attachment to a visor in a vehicle.

16. The apparatus as in claim 1, wherein the structure for attachment to a visor in a vehicle is configured and dimensioned for adjustable attachment to a visor in a vehicle.

17. The apparatus as in claim 1, the structure for attachment to a visor in a vehicle including a motorized system for moving at least a portion of the apparatus into and out of the field of view of the optical element, the structure for attachment to a visor in a vehicle being configured and dimensioned for adjustable attachment.

* * * * *